United States Patent
Ichikawa et al.

(10) Patent No.: US 8,684,989 B2
(45) Date of Patent: Apr. 1, 2014

(54) WEARING ARTICLE HAVING FASTENERS WITH FOLDING GUIDES

(75) Inventors: Makoto Ichikawa, Kagawa (JP); Naoto Ohashi, Kagawa (JP)

(73) Assignee: Unicharm Corporation, Ehime (JP)

( * ) Notice: Subject to any disclaimer, the term of this patent is extended or adjusted under 35 U.S.C. 154(b) by 446 days.

(21) Appl. No.: 12/744,779

(22) PCT Filed: Aug. 15, 2008

(86) PCT No.: PCT/JP2008/064630
§ 371 (c)(1),
(2), (4) Date: Oct. 13, 2010

(87) PCT Pub. No.: WO2009/069342
PCT Pub. Date: Jun. 4, 2009

(65) Prior Publication Data
US 2011/0022021 A1    Jan. 27, 2011

(30) Foreign Application Priority Data
Nov. 26, 2007    (JP) ................................. 2007-304954

(51) Int. Cl.
*A61F 13/15*    (2006.01)

(52) U.S. Cl.
USPC ...................... 604/391; 604/385.01; 604/380

(58) Field of Classification Search
USPC ........ 604/379, 380, 385.01, 385.03, 386–392
See application file for complete search history.

(56) References Cited

U.S. PATENT DOCUMENTS

| | | | | |
|---|---|---|---|---|
| 5,324,279 A | * | 6/1994 | Lancaster et al. | 604/391 |
| 6,454,751 B1 | * | 9/2002 | Olson | 604/391 |
| 7,198,621 B2 | * | 4/2007 | Moser et al. | 604/385.22 |

FOREIGN PATENT DOCUMENTS

| | | |
|---|---|---|
| JP | 5-65321 | 8/1993 |
| JP | 10-155834 | 6/1998 |
| JP | 2002-532147 | 10/2002 |
| JP | 2003-070833 | 3/2003 |
| WO | WO 00/35398 | 6/2000 |

OTHER PUBLICATIONS

International Search Report from corresponding PCT application No. PCT/JP2008/064630, dated Nov. 18, 2008, 4 pages.

* cited by examiner

*Primary Examiner* — Michele M Kidwell
(74) *Attorney, Agent, or Firm* — Brinks Gilson & Lione (57) ABSTRACT

A wearing article having a front waist region that is provided along a pair of opposite side edges with first fastening members, and a rear waist region provided along a pair of opposite side edges with second fastening members for engaging the first fastening members. Each of the second fastening members is formed with an uneven structure having a plurality of crests extending in a transverse direction and spaced one from another in a longitudinal direction. When the uneven structure comes into contact with the first fastening member, the resulting engagement is extremely weak and the uneven structure can be easily disengaged from the first fastening member. The uneven structure may be unfolded in the longitudinal direction and put in close contact with the first fastening member to achieve firm engagement over an area as large as possible between the flattened uneven structure and the first fastening member.

1 Claim, 7 Drawing Sheets

WEARING ARTICLE HAVING FASTENERS WITH FOLDING GUIDES

RELATED APPLICATION

This application is a 35 U.S.C. §371 national phase filing of International Patent Application No. PCT/JP2008/064630, filed Aug. 15, 2008, through which and to which priority is claimed under 35 U.S.C. §119 to Japanese Patent Application No. 2007-304954, filed Nov. 26, 2007.

TECHNICAL FIELD

The present invention relates to wearing articles and particularly to wearing articles such as disposable diapers, toilet-training pants, incontinent briefs, or diaper covers and the like.

RELATED ART

Disposable diapers having front and rear waist regions detachably fastened together along transversely opposite side edges of diapers is known, for example, from the disclosure of JP 2002-532147W. According to the disclosure of JP 2002-532147W, a diaper comprises a liquid-absorbent chassis which comprises, in turn, front and rear waist regions, a crotch region and the inner side facing the wearer's skin and the outer side facing the wearer's garment, and hook elements and loop elements provided along the side edges of the front and rear waist regions. Specifically, the loop elements are provided on the outer side facing the garment of the front waist region along its transversely opposite side edges and the hook elements are provided on the inner side facing the wearer's skin of the rear waist region along its transversely opposite side edges so that these loop and hook elements may be engaged together to make the diaper in a pant-shape.
Patent Document 1: JP 2002-532147W

DISCLOSURE OF THE INVENTION

Problem to be Solved by the Invention

According to the disclosure, the hook and loop elements extend in a longitudinal direction along the transversely opposite side edges of the front and rear waist regions, respectively. Lengths of the hook and loop elements are dimensioned to be substantially equal to lengths of the respective side edges to enlarge the area over which these elements are engaged one with another and thereby to enhance the fastening effect. Operation of engaging the hook and loop one with another is carried out, for example, as will be described. Such operation is started by engaging the longitudinally upper end of the hook element with associated upper end of the loop element for positioning followed by engaging the remaining portions of the respective elements with one another. However, the longitudinally lower portions of the respective elements should be unintentionally engaged with one another in the course of positioning the upper ends, resulting in a misaligned engagement. To remedy this, the unintentionally engaged portions must be disengaged from each other and it must be tried to engage again these portions with each other so as to assure the proper positioning, i.e., the proper alignment. In this regard, the fastening means adopted by the disposable diaper cited above has left unsolved a problem such that time and labor should be taken for handling of the fastening means. This problem has been significant particularly in the adult diaper of large size.

In view of the problem as has been discussed above, the present invention provides a wearing article improved so that the front waist region and the rear waist region can be easily and normally engaged with each other.

Measure to Solve the Problem

According to the present invention, there is provided an wearing article comprising a liquid-absorbent chassis having a longitudinal direction, a transverse direction, an inner side facing the wearer's skin, an outer side facing the wearer's garment, a front waist region, a rear waist region and a crotch region extending between the front and rear waist region, and fastening means adapted to detachably fasten the front and rear waist regions to each other along respective pairs of side edges thereof opposed in the transverse direction and extending in the longitudinal direction.

The present invention is characterized in that the fastening means comprise first fastening members lying inside as viewed in a circumferential direction and second fastening members lying outside as viewed in the circumferential direction when joining the front and rear waist regions to each other, the first fastening members are attached to the side edges so as to extend in the longitudinal direction and respectively have inner and outer side edges opposed in the transverse direction, the second fastening members are attached to the side edges so as to extend in the longitudinal direction and respectively have inner and outer side edges opposed in the transverse direction in a manner that the second fastening members are detachably engaged with associated the first fastening members, and the second fastening members and the side edges to which the second fastening members are attached are provided with folding guide means serving to facilitate the second fastening members to be folded along foldable regions defined by the folding guide means.

According to one preferred embodiment, the foldable region extends from the outer side edge to the inner side edge in a manner that, between said foldable region and a line orthogonal to a longitudinal center line bisecting of the second fastening member in said transverse direction, an angle of 30 to 60° is included.

According to another preferred embodiment, the second fastening member includes upper and lower ends opposed to each other in the longitudinal direction and extending in the transverse direction, and the foldable region including an end lying on the outer side edge and an end lying on the inner side edge, wherein the end lying on the outer side edge is put aside toward the upper end relative to the end lying on the inner side edge so that the foldable region extends obliquely from the former end on the outer side edge to the latter end on the inner side edge.

According to still another preferred embodiment, the folding guide means is formed by heat processing.

According to yet another preferred embodiment, the folding guide means comprises a slit distributed region.

According to further another preferred embodiment, the folding guide means comprises a separator region defined by partially cutting out the second fastening member.

According to an additional preferred embodiment, the folding guide means comprises a high stiffness member attached to the second fastening member.

Effect of the Invention

The folding guide means provided in the second fastening member ensures that the upper region of the second fastening member can be put in engagement with the first fastening member while the second fastening member is maintained in the folded state. After the upper region of the second fastening member has been engaged with the first fastening member, the lower region may be unfolded back and this lower region may be put in engagement with the first fastening member. In this way, the lower region of the second fastening member should not be unintentionally engaged with the first fastening member in the course of engaging the upper region of the second fastening member with the first fastening member.

The foldable region extends at an angle α of 30 to 60° with respect to the line orthogonal to the longitudinal center line of the second fastening member and the second fastening member may be folded along this foldable region. In this way, the second fastening member can be smoothly folded and can be well maintained in the folded position.

The end of the foldable region lying on the outer side edge is aside upward from the end lying on the inner side edge, resulting in that the foldable region obliquely extends downward from the outer side edge to the inner side edge. In this way, the second fastening member with its lower region folded outward can be smoothly put in engagement with the first fastening member.

IDENTIFICATION OF REFERENCE NUMERALS USED IN THE DRAWINGS

Description of the Best Mode for Working of the Invention

<First Embodiment>

Figure 1:
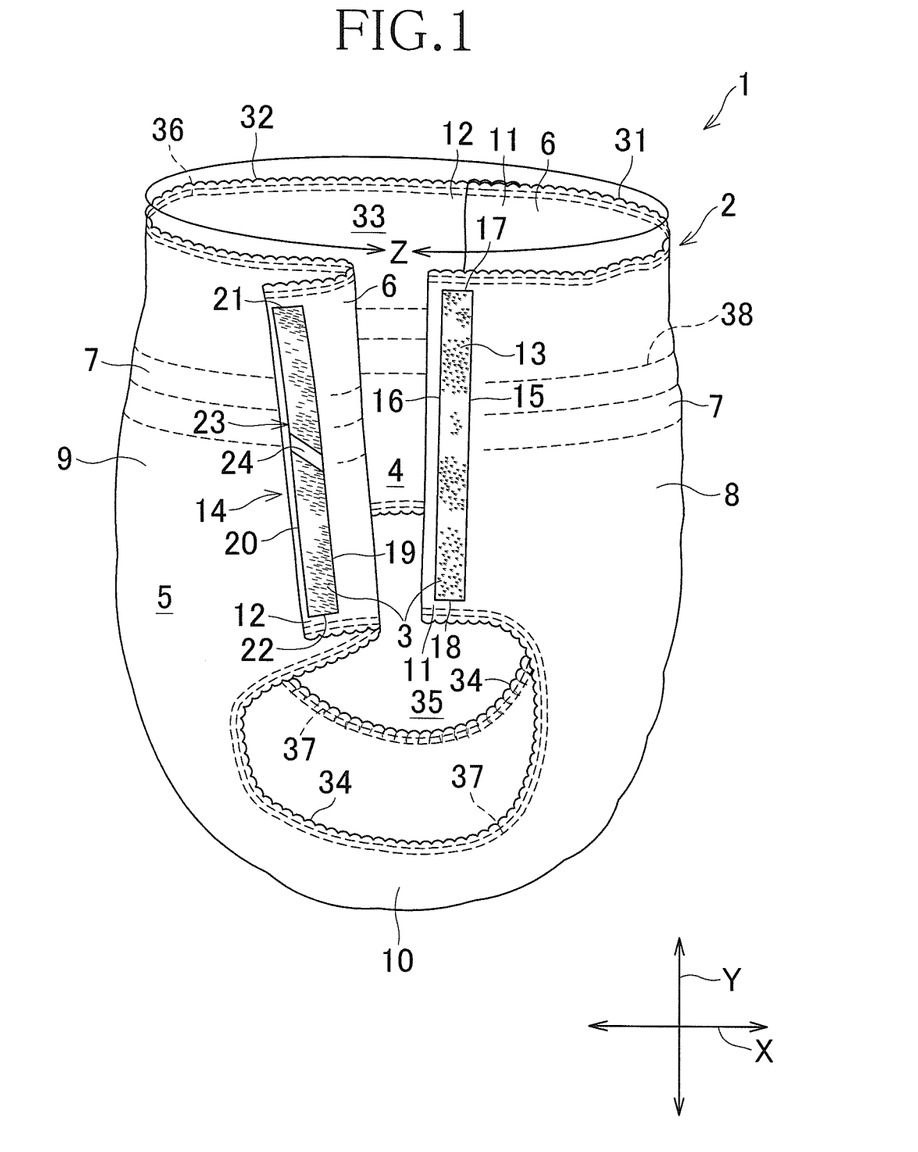
FIG. 1 is a perspective view showing a first embodiment of a diaper according to the present invention.

FIGS. 1 through 4 illustrate a first embodiment according to the present invention in the form of a diaper for adult as one example. As seen in FIG. 1, a diaper 1 comprises a liquid-absorbent chassis 2 and fastening means 3. The chassis 2 has a longitudinal direction Y, a transverse direction X, a circumferential direction Z, an inner side 4 facing the wearer's skin and an outer side 5 facing the wearer's garment. The chassis 2 comprises an inner sheet 6 defining the inner side 4 facing the wearer's skin, an outer sheet 7 defining the outer side 5 facing the wearer's garment and a liquid-absorbent core (not shown) interposed between these inner and outer sides 6, 7. The inner sheet 6 may be formed, for example, from a liquid-pervious nonwoven fabric, the outer sheet 7 may be formed, for example, from a liquid-impervious film and the liquid-absorbent core may be formed, for example, from a mixture of fluff pulp and super-absorbent polymer particles. Generally, materials for these components may be selected from those conventionally used in the relevant technical field. The chassis 2 configurationally comprises a front waist region 8, a rear waist region 9 and a crotch region 10 sandwiched between the front and rear waist regions 8, 9.

The front waist region 8 includes a pair of side edges 11 opposed to each other in the transverse direction X and extending in the longitudinal direction Y and the rear waist region 9 includes a pair of side edges 12 opposed to each other in the transverse direction X and extending in the longitudinal direction Y. The outer sheet 7 is provided along the side edges 11 of the front waist region with first fastening members 13 comprising loop elements attached thereto by use of adhesive or welding technique.

The inner sheet 6 is provided along the side edges 12 of the rear waist region with second fastening members 14 comprising hook elements adapted to be detachably engaged with the first fastening members 13 wherein these second fastening members 14 also may be attached thereto by use of adhesive or welding technique. The first fastening members 13 cooperate with the associated second fastening members 14 to provide fastening means 3 according to the second aspect of the present invention.

Figure 2:
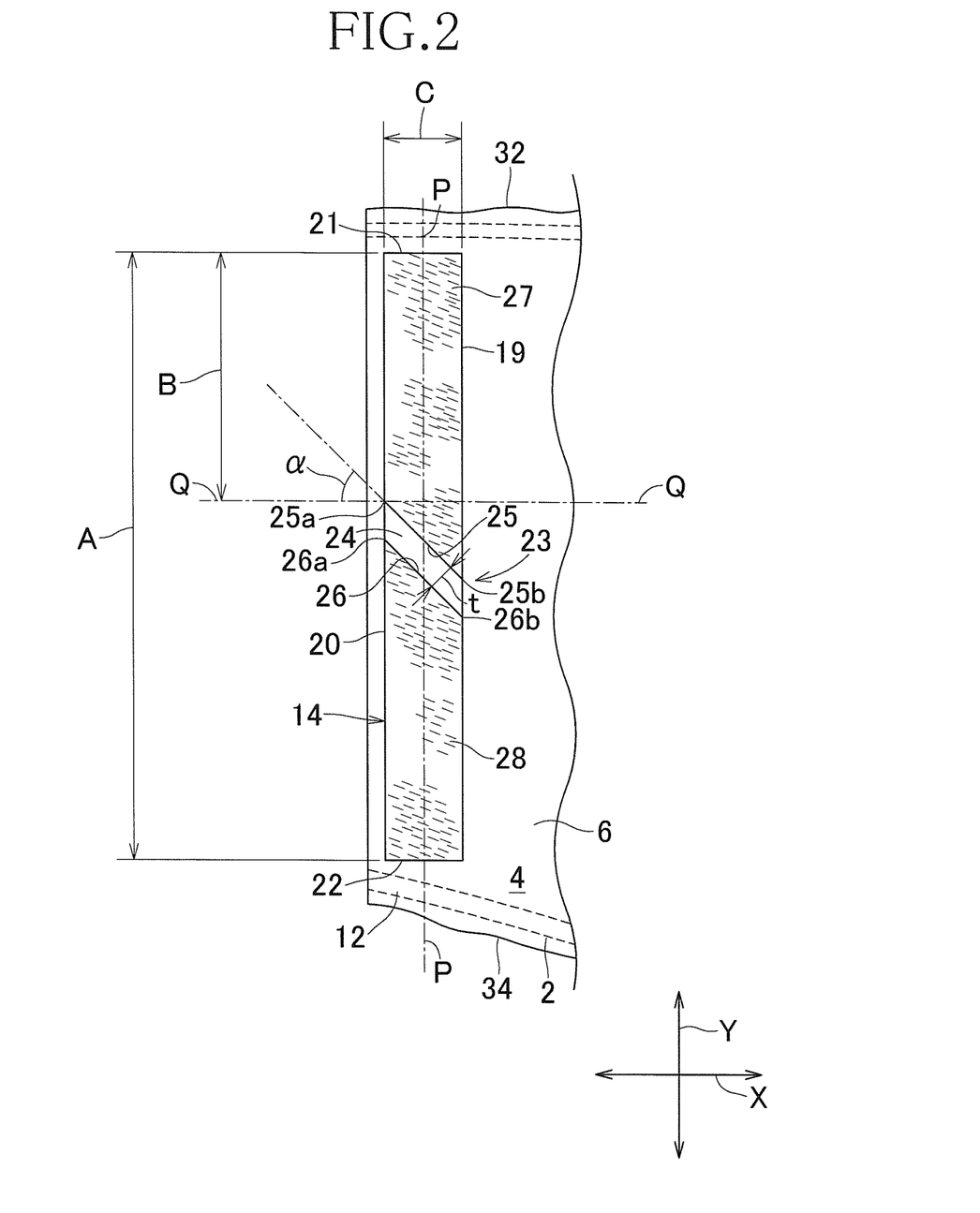
FIG. 2 is a diagram illustrating details of the second fastening element.

The first and second fastening members 13, 14 have substantially the same dimensions as those of the side edges 21, 22 of the front and rear waist regions, respectively, as measured in the longitudinal direction. The first fastening member 13 includes inner and outer side edges 15, 16 opposed to each other in the transverse direction X and extending in the longitudinal direction Y and upper and lower ends 17, 18 opposed to each other in the longitudinal direction Y and extending in the transverse direction X. The second fastening member 14 includes inner and outer side edges 19, 20 opposed to each other in the transverse direction X and extending in the longitudinal direction Y and upper and lower ends 21, 22 opposed to each other in the longitudinal direction Y and extending in the transverse direction X. The inner side edges 15, 19 are placed aside from the outer side edges 16, 20 inwardly of the chassis 2 as viewed in the transverse direction X.

FIG. 2 illustrates details of a second fastening member 14. As illustrated, the second fastening member 14 is formed with a folding guide means 23 facilitating the second fastening member 14 to be folded. The second fastening member 14 is a thermoplastic member formed from a polyolefin resin, particularly a mixture of polypropylene and polyethylene. The folding guide means 23 includes a foldable region 24 formed by heat processing the second fastening member 14. The foldable region 24 obtained by heat processing the second fastening member 14 having a thermal plasticity has a relatively high stiffness and a relatively thin thickness in comparison to the remaining region not subjected to heat processing. Such differential stiffness and thickness facilitate this foldable region 24 to be folded.

The foldable region 24 comprises an upper fold line 25 placed aside toward the upper end 21 and a lower fold line 26 placed aside toward the lower end 22 so that the second fastening member 14 may be folded between the upper fold line 25 and the lower fold line 26. A dimension t measured from the upper fold line 25 to the lower fold line 26 is in a range of about 3 to 20 mm. If the dimension t is less than about 3 mm, the dimension t will be narrower than the thickness of the second fastening member 14 and it will be difficult to fold the second fastening member 14 smoothly. If the dimension t exceeds about 20 mm, on the contrary, a region free from engagement with the first fastening member 13 will become unacceptably large and, in consequence, the front and rear waist regions 8, 9 will be apt to be unfastened from each other.

The upper and lower fold lines 25, 26 respectively extend from the outer side edge 20 to the inner side edge 19 and respectively include ends 25a, 26a lying on the outer side edge 20 and ends 25b, 26b lying on the inner side edge 19. The upper and lower fold lines 25, 26 extend substantially in parallel to each other and the ends 25a, 26a on the outer side edge 20 are placed aside from the ends 25b, 26b on the inner side edge 19 toward the upper end 21. Specifically, the foldable region 24 obliquely extends with respect to the longitudinal center line P-P bisecting the second fastening member 14 in the transverse direction X. More specifically, the foldable region 24 extends at an angle α preferably of 30 to 60° and most preferably of about 45° with respect to extension of the line orthogonal to the longitudinal center line P-P.

A dimension A of the second fastening member 14 as measured from the upper end 21 to the lower end 22 in the longitudinal direction Y is about 130 mm and a dimension B as measured from the upper end 21 to the end 25a lying on the outer side edge 20 is about 10 to 50 mm. A dimension C of the second fastening member 14 as measured from the inner side edge 19 to the outer side edge 20 is about 15 mm. It should be understood here that may be appropriately varied depending on the diaper's size these dimensions and the types of materials to be used.

The second fastening member 14 is divided, about the foldable region 24 defining the boundary, in an upper region 27 lying on the side of the upper end 21 and a lower region 28 lying on the side of the lower end 22.

Figure 3:
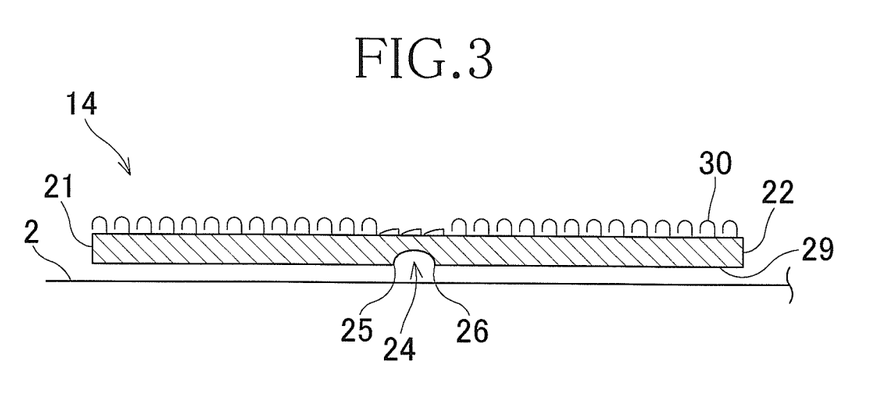
FIG. 3 is a sectional view taken along a longitudinal center line P-P in FIG. 2.

FIG. 3 is a sectional view taken along the longitudinal center line P-P in FIG. 2. The second fastening member 14 is heated at a temperature of about 120° C. under a pressure from the side on which the second fastening member 14 has been bonded to the chassis 2. Being thermoplastic, the second fastening member 14 is locally fused so as to form a concave groove as it is heated under pressure. At the same time, a hook forming surface 30 of the second fastening member 14 is also pressurized and the hook elements are locally collapsed. An area of the second fastening member 14 locally heated and pressurized defines the foldable region 24. The foldable region 24 has a higher stiffness and a thinner thickness than the remaining region. In consequence, the second fastening member 14 can be easily folded along this foldable region 24.

These first and second fastening members 13, 14 may be engaged together to join the front waist region 8 with the rear waist region 9 and thereby to obtain the diaper 1 of pant-type as shown in FIG. 1. In the diaper 1 of pant-type, a waist-opening 33 is defined by respective upper edges 31, 32 of the front and rear waist regions 8, 9, i.e., these edges cooperating with each other to define a peripheral edge of the waist-opening 33 and a pair of leg-openings 26 defined by transversely opposite side edges 34, 34 of the crotch region 10, i.e., the edges adapted to define peripheral edges of the respective leg-openings 35. The front and rear halves 31, 32 of the waist-opening's peripheral edge are provided with waist elastic members 36 attached thereto under tension so as to extend along these halves of 31, 32 of the waist-opening's peripheral edge. The leg-openings' peripheral edges 34 are provided inside thereof with leg elastic members 37 attached thereto under tension so as to extend along these peripheral edges 34, respectively. Both the waist elastic members 36 and the leg elastic members 37 comprise a plurality of rubber strings so that s desired fit of the front and rear halves 31, 32 of the waist-opening's peripheral edge and of the respective leg-openings' peripheral edges 34 may be assured by a contractile force of these rubber strings.

The front and rear waist regions 8, 9 are provided at substantially middle levels as viewed in the longitudinal direction Y with auxiliary elastic members 38 attached thereto under tension to improve fitness of the diaper to the wearer's body. The auxiliary elastic member 38 extends around the wearer's waist in a circumferential direction Z and comprises a plurality of rubber strings arranged to be spaced one from another in the longitudinal direction Y so that a contractile force of these rubber strings may ensure the front and rear waist regions to fit to the wearer's body at the respective middle levels of the front and rear waist regions 8, 9 thereof.

For the waist elastic member 36, the leg elastic member 37 and the auxiliary elastic member 38, natural rubber or synthetic rubber such as that made of polyurethane may be used and it is possible to implement these elastic members in the form of an elasticized fibrous nonwoven fabric or elasticized plastic sheet instead of the rubber strings.

Figure 4:
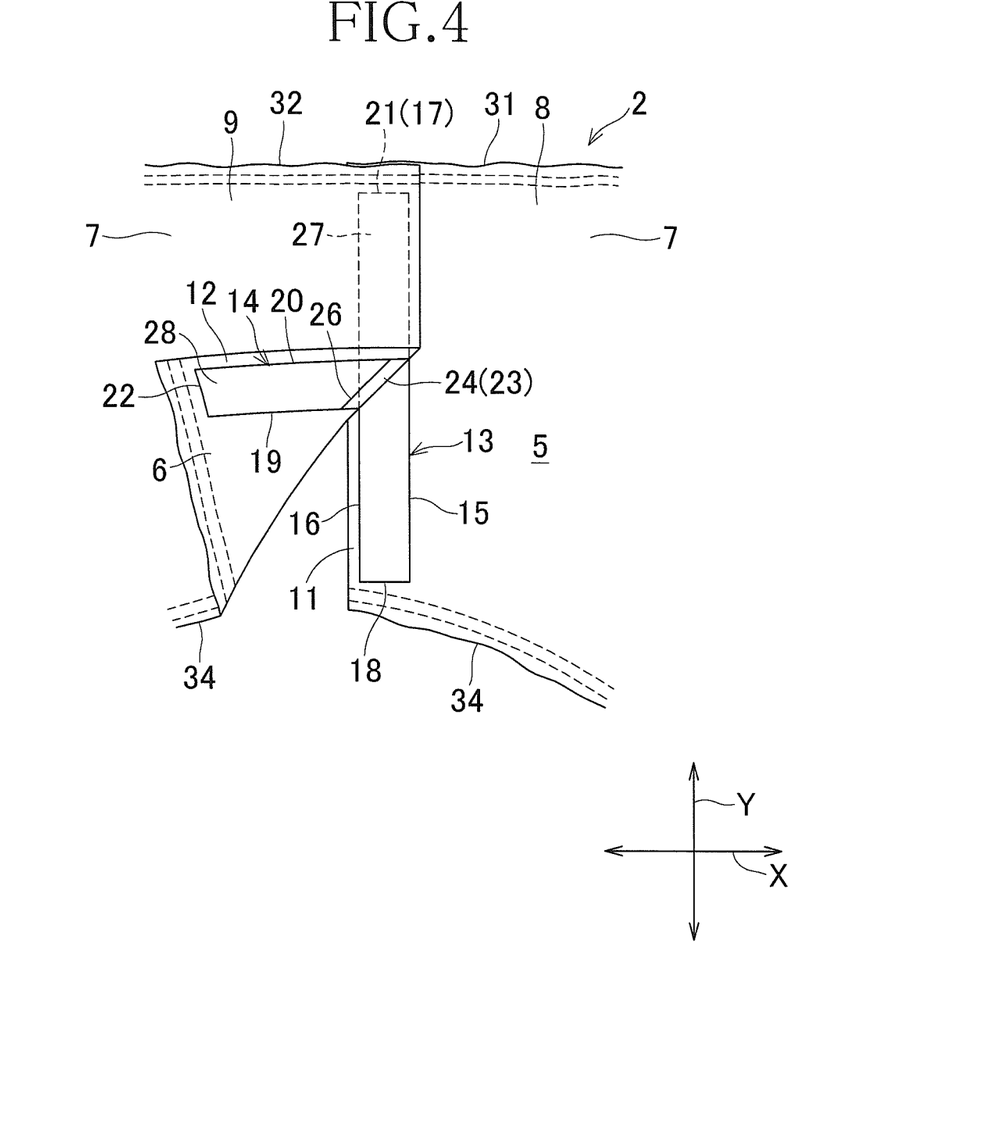
FIG. 4 is a diagram illustrating front and rear waist regions as engaged one with another.

In the diaper 1, the first fastening members 13 and the second fastening members 14 are engaged with each other in such a manner as will be described with reference to FIG. 4. Each of the second fastening members 14 lying outside as viewed in the circumferential direction Z is put in engagement with the associated first fastening member 13 lying inside as viewed in the circumferential direction Z, i.e., lying on the side of the wearer' body. For operation of such engagement, the second fastening member 14 may be previously folded along the foldable region 24. A differential stiffness as well as a differential thickness between the foldable region 24 and the remaining region facilitates the second fastening member 14 to be folded along this foldable region 24. The foldable region 24 obliquely extends downward from the outer side edge 20 to the inner side edge 19 and such feature also facilitates the lower region 28 to be folded outward in the circumferential direction Z. The lower region 28 can be folded outward easier than inward in the circumferential direction Z. Thereby it is possible to prevent the lower region 28 from unintentionally being engaged with the first fastening member 13 and furthermore to protect the wearer's skin from being injured by the hook elements on the lower region 28.

As has previously been described, the foldable region 24 extends preferably at an angle α of about 30 to 60° with respect to the line Q-Q. If this angle α is set to be smaller than about 30°, it will be difficult to fold the lower region 28 neatly and eventually the lower region 28 will partially overlap the upper region 27. In addition to such inconvenience, the periphery 34 of the associated leg-opening will make it difficult to fold the lower region 28. If the angle α is set to be larger than about 60°, a dimension in the longitudinal direction Y over which the upper region 27 is engaged with the first fastening member 13 will be substantially elongated and consequently it will be difficult to put the upper region 27 in accurate engagement with the first fastening member 13.

With the lower region 28 folded in this manner, the upper end 21 of the second fastening member 14 is aligned with the upper end 17 of the first fastening member 13 and then the upper region 27 of the second fastening member 14 is engaged with the first fastening member 23. Referring to FIG. 4, in the step of put the upper region 27 in engagement with the second fastening member 14, the lower region 28 should not be unintentionally engaged with the first fastening member 13 because the lower region 28 has been folded outward. Once the upper region 27 has been firmly engaged with the first fastening member 13, the lower region 28 may be unfolded to its initial position and then put in engagement with the first fastening member 13. In this step, it is ensured that the lower region 28 is reliably engaged with the first fastening member 13 at the desired position without any undesirable displacement because the upper region 27 has already been firmly engaged with the first fastening member 13. In this way, the presence of the folding guide means 23 assures that the second fastening member 14 can be easily and reliably engaged with the first fastening member 13.

As has previously been described, the dimension B as measured from the upper end 21 to the end 25a lying on the outer side edge of the second fastening member 14 is set in a range of about 10 to 50 mm. If the dimension B is shorter than 10 mm, engaging force between the upper region 27 and the first fastening member 13 will be too weak to maintain the upper region 27 in engagement with the first fastening member 13 in the course of engaging the lower region 28 with the first fastening member 13. If the dimension B is longer than about 50 mm, on the contrary, it will become difficult to put the upper region 27 in accurate engagement with the first fastening member 13.

Formation of the folding guide means 23 along each of the side edges 12 of the rear waist region is effective to improve a feeling to wear the diaper 1. With the diaper 1 put on the wearer's body also, the folding guide means 23 is more flexible in concert with movement of the wearer than the remaining part and deformable in conformity to the wearer' body. Without formation of the folding guide means 23, a stiffness of the first and second fastening members 13, 14 would deteriorate a feeling to wear.

While the first and second fastening members 13, 14 are described herein wherein the former includes the loop elements and the latter includes the hook elements, it is also possible that the first fastening member 13 includes the hook elements and the second fastening member 14 including the loop elements. However, it should be noted here that the hook elements usually have a stiffness higher than that of the loop elements. Taking account of this, it is preferred to press the hook elements having the higher stiffness against the loop elements and thereby to achieve a relatively confirm engagement. Fastening means 3 is not limited to such a combination of the first and second fastening members 13, 14 but the other means such as pressure-sensitive adhesive tape may be used so far as the front and rear waist regions 8, 9 can be detachably fastened together.

While formation of the folding guide means 23 are limited to the second fastening members 14 according to this embodiment, it is possible to form the first fastening members 13 also with the folding guide means 23. If both of the first and second fastening members 13, 14 are formed with the folding guide means 23, operation of engagement will be further easier. While the first fastening member 13 is attached directly to the outer sheet 7 and the second fastening member 14 is attached directly to the inner sheet 6 according to this embodiment, it is also possible to prepare separate retaining sheets for these fastening members and to attach these retaining sheets to the inner sheet 6 or the outer sheet 7.

While the second fastening members 14 are attached to the side edges 12 of the rear waist region after the second fastening members 14 have been formed with the folding guide means 23 according to this embodiment, it is also possible to form the folding guide means 23 after the second fastening members 14 have been attached to the side edges 12 of the rear waist region.

<Second Embodiment>

Figure 5:
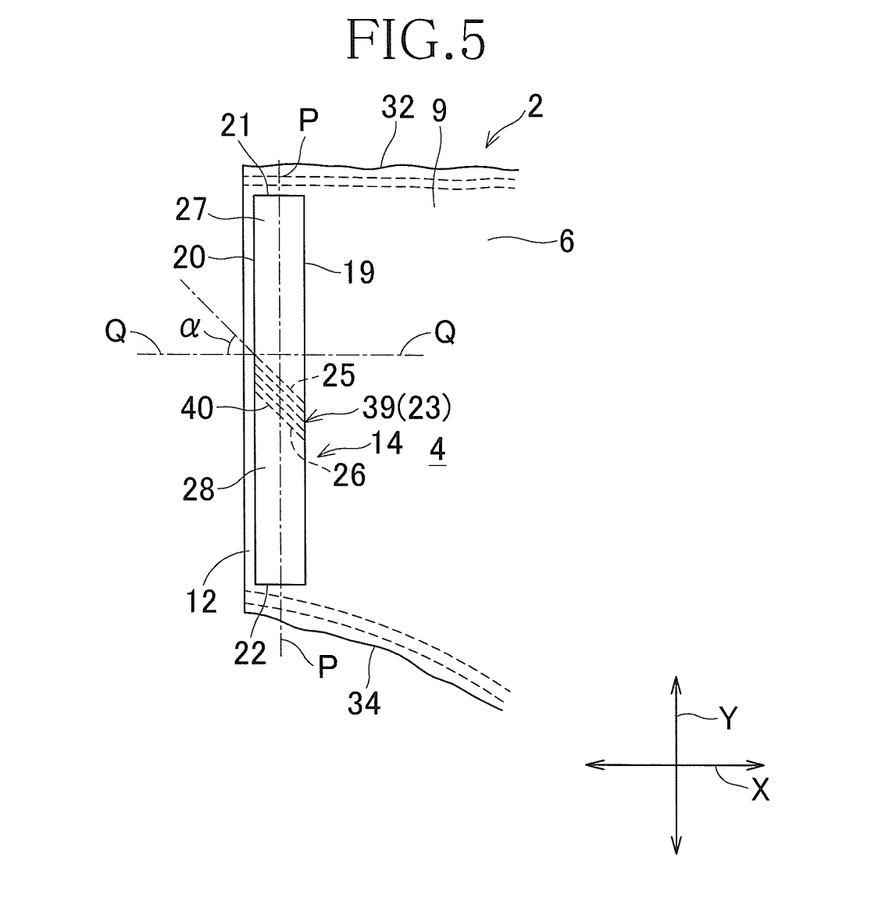
FIG. 5 is a diagram partially illustrating a second embodiment according to the present invention.

FIG. 5 illustrates a second embodiment according to the present invention wherein the inner side 4 of the diaper 1 faces the wearer's skin. This second embodiment is distinguished from the first embodiment with respect to the folding guide means 23 and the other components are similar to those in the first embodiment. The similar components will not be described repetitively.

According to this embodiment, the folding guide means 23 are implemented in the form of slit distributed region 39 provided in the second fastening members 14 and the side edges 12 of the rear waist region in the chassis 2.

The slit distributed region 39 comprises five slit rows 40 arranged substantially in parallel one to another wherein each row includes a plurality of slits arrange at regular intervals. The individual slit constituting each of the slit rows 40 has a length of about 3 mm and a distance between each pair of the adjacent slits is about 3 mm. The slit distributed region 39 is formed, for example, by feeding the side edges 12 of the rear waist region in the chassis 2 together with the second fastening members 14 attached to the respective side edges 12 to a gear mechanism provided with a cutter.

Location of the folding guide means 23 in the form of the slit distributed region 39 is the same as in the first embodiment. The angle a of the foldable region 24 is defined by an angle included between the extension of the single slit row 40 and the line Q-Q.

The slit distributed region 39 exhibits a reduced stiffness in comparison to the remaining region and correspondingly more flexible than the remaining region. Consequentially, the upper region 27 can be put in engagement with the first fastening member 13 after the lower region 28 has been folded outward and thereby the second fastening member 14 can be easily and reliably engaged with the first fastening member 13.

While the slit rows 40 are formed after the second fastening member 14 has been attached to the chassis 2 according to this embodiment, it is also possible to attach the second fastening members 14 to the chassis 2 after the second fastening members 14 have been formed with the slit rows 40. In this case, the slit rows 40 are formed only in the second fastening members 14 and the chassis 2 is formed with none of the slit rows 40.

The dimension of the individual slit and the number of the slit rows 40 are not limited to this embodiment and may be appropriately selected.

Figure 6:
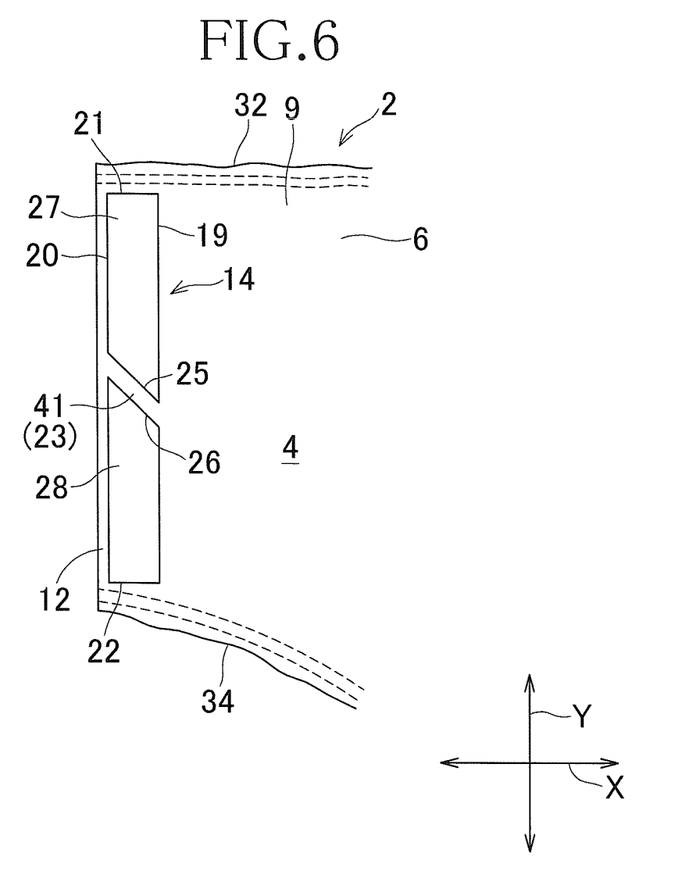
FIG. 6 is a diagram partially illustrating a third embodiment according to the invention.

FIG. 6 illustrates a third embodiment according to the present invention wherein the folding guide means 23 may be implemented in the form of a separator region 41 separating the upper region 27 and the lower region 28 of the second fastening member 14 from each other. The other components are similar to those in the first embodiment and will not be described repetitively.

In the separator region 41, the second fastening member 14 is partially cut out to form the folding guide means 23. In the second fastening member 14, the upper fold line 25 is formed on the side of the upper region 27 and the lower fold line 26 is formed on the side of the lower region 28 about the separator region 41. Location of the folding guide means 23 is similar to the case of the first embodiment.

According to this embodiment, the second fastening member 14 is not present in the separator region 41 defining the folding guide means 23, allowing a stiffness of the separator region 41 to be reduced in comparison to the remaining region. In consequence, the second fastening member 14 can be easily folded about the separator region 41.

Figure 7:
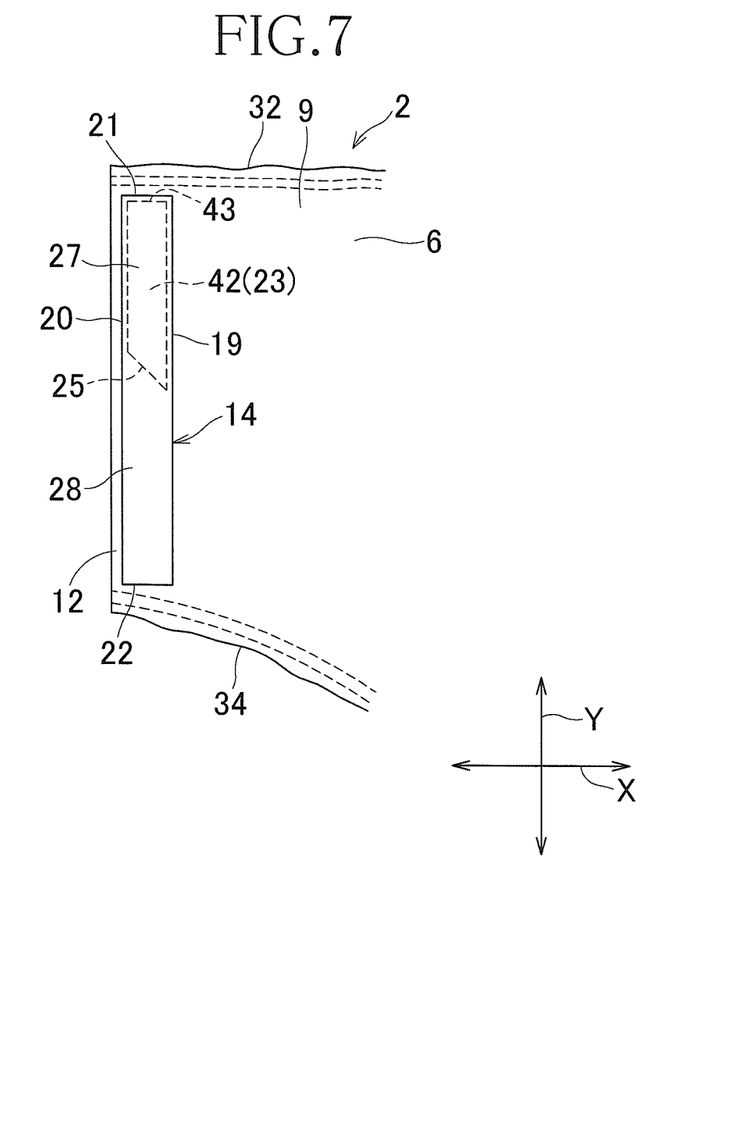
FIG. 7 is a diagram partially illustrating a fourth embodiment according to the present invention.

FIG. 7 illustrates a fourth embodiment according to the present invention wherein the folding guide means 23 comprises a high stiffness member 42 provided in the upper region 27 of the second fastening member 14. The other components are similar to those in the first embodiment and will not be described repetitively.

The high stiffness member 14 may be formed, for example, by a sheet member such as a nonwoven fabric, woven fabric or film and interposed between the second fastening member 14 and the inner sheet 6.

The high stiffness member 42 has its upper end 43 substantially in conformity with the upper end 21 of the second fastening member 14 and its lower end serving as the upper fold line 25. It will be appreciated that the upper fold line 25 serves also as the lower fold line 26 which is not formed in this embodiment.

According to this embodiment, the upper region 27 is defined by the second fastening member 14 and the high stiffness member 42 while the lower region 28 is defined by the second fastening member 14 alone. With such a unique arrangement, a differential stiffness between these upper and lower regions 27, 28 facilitates the second fastening member 14 to be folded about the upper fold line 25.

While the high stiffness member 42 is provided over the entire upper region 27 according to this embodiment, it is possible to provide the high stiffness member 42 only in the vicinity of the upper fold line 25. It is also possible to provide the high stiffness member 42 on the side of the lower region 28 so as to generate a differential stiffness between the lower region 28 and the upper region 27.

The invention claimed is:

1. A wearing article comprising:
a liquid-absorbent chassis having a longitudinal direction, a transverse direction, an inner side facing the wearer's skin, an outer side facing the wearer's garment, a front waist region, a rear waist region and a crotch region extending between the front and rear waist region; and
fastening means adapted to detachably fasten said front and rear waist regions to each other along respective pairs of side edges thereof opposed in said transverse direction and extending in said longitudinal direction, wherein:
said fastening means comprise first fastening members lying inside as viewed in a circumferential direction and second fastening members lying outside as viewed in said circumferential direction when joining said front and rear waist regions to each other;
said first fastening members are attached to said side edges so as to extend in said longitudinal direction and respectively have inner and outer side edges opposed in said transverse direction;
said second fastening members are attached to said side edges so as to extend in said longitudinal direction and respectively have inner and outer side edges opposed in said transverse direction in a manner that said second fastening members are detachably engaged with associated said first fastening members;
said second fastening members and said side edges to which said second fastening members are attached are provided with folding guide means serving to facilitate said second fastening members to be folded along foldable regions defined by said folding guide means,
said second fastening member includes upper and lower ends opposite to each other in the longitudinal direction and extending in the transverse direction;
said foldable region includes an end lying on said outer side edge and an end lying on said inner side edge, wherein said end lying on said outer side edge is closer to said upper end relative to said end lying on said inner side edge so that said foldable regions extends as a continuous structure in an oblique orientation with respect to a longitudinal center line that bisects the second fastening member in the transverse direction;
said foldable region extends from said outer side edge to said inner side edge in a manner that said foldable region and a line orthogonal to the longitudinal center line bisecting the second fastening member in the transverse direction form an angle of 30° to 60°; and
said folding guide means is formed by heat processing.

* * * * *